United States Patent [19]

Mojonnier

[11] Patent Number: Plant 7,681

[45] Date of Patent: Oct. 22, 1991

[54] ALSTROEMERIA PLANT NAMED MARGARITA

[76] Inventor: Erwin Mojonnier, 237 Quail Dr., Encinitas, Calif. 92024

[21] Appl. No.: 556,403

[22] Filed: Jul. 24, 1990

[51] Int. Cl.[5] ..... A01H 5/00

[52] U.S. Cl. ..... Plt./68

[58] Field of Search ..... Plt. 68, 87.1

*Primary Examiner*—Howard J. Locker

*Attorney, Agent, or Firm*—Foley & Lardner

[57] ABSTRACT

An Alstroemeria plant named Margarita, characterized by its early winter production in early December, few non-flowering stems per plant, ease of propagation, excellent post-harvest color retention, and by its red-purple background color, with grayed-purple streaks and yellow spots on the upper petals.

1 Drawing Sheet

The present invention relates to a new and distinct cultivar of Alstroemeria plant hereinafter referred to by the cultivar name Margarita.

Margarita is a product of a planned breeding program which had the primary objectives of creating new Alstroemeria cultivars having unique flower color and being capable of early winter production with low maintenance requirements. The latter term refers to the production of a minimum of non-flowering stems. Such traits in combination were not present in previously available commercial cultivars.

In order to fully understand an important characteristic of the new cultivar, an explanation of typical current winter production schedules for cut flowers of Alstroemerias would be helpful. Standard industry growing practices normally utilize only natural daylight. As a result, late fall and winter production of Alstroemeria cut flowers, due to reduced levels of light during these periods, typically requires 12 weeks or more of growing time from the planting of the rhizome cutting to the initiation of flowering. Even more time is required for further flowering to produce a stem ready to sale. With certain varieties, the period of time from planting to flowering can extend up to almost six months. This time will substantially vary from variety to variety, and growing techniques and conditions also affect the growing period. For example, a larger cutting will obviously require a shorter growing time than a relatively small cutting. High temperatures normally have an adverse affect on growth, as does reduced light.

The commercial implications of relatively slow growth characteristics under natural light conditions should be obvious. Increased bench or field time (if grown outdoors where climates permit) substantially increases production costs, which in turn result in increased costs per stem due to the increased cost of production. Total production of Alstroemeria cut flowers during such period is also correspondingly less. This adversely affects the normal supply/demand ratio in the marketplace, and as a result cut flowers of Alstroemeria are substantially more costly during the winter months than during the periods beginning in March when production increases. It is not unusual for stem prices to be 50% higher during the winter months of December, January and February.

The inventor has discovered that through photoperiodic growth practices, certain cultivars can be brougth into flowering in the late fall and winter periods in substantially reduced periods of time, thereby increasing production during these periods. However, all cultivars are not adaptable to photoperiodic control.

Through extensive breeding, the inventor has been able to produce new Alstroemeria cultivars, of which Margarita is one, specifically adaptable to photoperiodic control. The inventor's preferred growing technique includes growing the newly stuck plants under natural light conditions for approximately one month without light supplement. After approximately one month, the day length is effectively increased by providing four hours of artificial lighting by techniques or methods well known in the industry.

A preferred growing regimen which has provided excellent results comprises planting established rhizome divisions in ground beds near the end of August or first of September. Beginning approximately one month after planting, and continuing to April 1, the plants are subjected to light from 2:00 a.m. to 6:00 a.m. daily. A lighting system which has proved highly effective consists of 135 watt bulbs spaced every 10 feet, and hung approximately 7 feet above the ground. The bulbs are positioned in rows that are spaced 12 feet apart.

By effectively increasing the day length by means of artificial lighting, flowering can be initiated in a much shorter time. Within approximately six (6) weeks the first flower appears, and saleable stems are ready from mid-November to mid-December, depending upon the variety. In many instances, flowering is essentially continuous until June when the stems are too short to sell as cuts without heavy shading and some method of cooling. Without shading and cooling to prolong commercial stem production, it is common practice to dig up and divide the plants. The divided plants are then stuck in late August or early September as described, and the cycle repeated. It has also been noted that the increased light regimen has resulted in longer stems, a very desirable quality.

Margarita was originated by the inventor Erwin Mojonnier from a hybridization made in a controlled breeding program in Encinitas, Calif. in 1988. The female parent was a cultivar identified as L4, a tall plant with a red flower having streaking on the upper and lower petals, and with a yellow patch on the upper petals. The male parent of Margarita was a cultivar identified as L2, a short plant, with a flower having a light pink background with a dark pink cheek. Streaking appears on the upper and lower petals, with a yellow patch appearing on the upper petals.

Margarita was discovered and selected as one flowering plant within the progeny of the stated parentage by Erwin Mojonnier in May 1988 in a controlled environment in Encinitas, Calif.

The first act of asexual reproduction of Margarita was accomplished when vegetative cuttings were taken from the initial selection in August 1988 in a controlled environment in Encinitas, Calif. by Erwin Mojonnier. Horticultural examination of selected units initiated in 1989 has demonstrated that the combination of characteristics as herein disclosed for Margarita are firmly fixed and retained through successive generations of asexual reproduction.

Margarita has not been observed under all possible environmental conditions. The phenotype may vary significantly with variations in environment such as temperature, light intensity and day length. The following observations, measurements and comparisons describe plants grown in Encinitas, Calif. under greenhouse conditions which approximate those generally used in commercial practice.

The following traits have been repeatedly observed and are determined to be basic characteristics of Margarita, which in combination distinguish this Alstroemeria as a new and distinct cultivar:

1. Low maintenance, with few non-flowering stems being produced per plant.

2. Margarita is responsive to increased light for initiating flowering. By effectively increasing day length by artificial light in optimum amounts, the first flower appears approximately six weeks after rhizome planting, and saleable stems in full flower are ready by early December. Thus, winter production can begin relatively early and, through photoperiodic control, continue throughout the winter period. Production can therefore be effectively staggered continuously through winter periods of low natural light.

3. Margarita is easily propagated by rhizome cuttings.

4. Margarita has a red-purple main flower color, heavy grayed-purple markings on the upper two petals, fewer markings on the lower petal, and a yellow spot on the upper petals.

5. Margarita has excellent post-harvest color retention of approximately 14 days.

The accompanying color photographic drawing shows typical inflorescence and foliage characteristics of Margarita, with colors being as nearly true as possible with illustrations of this type. The photograph comprises an enlarged close-up of an open flower of Margarita. The flower parts and colors referred to below are clearly shown in the photograph.

In the following description, color references are made to The Royal Horticultural Society Colour Chart (R.H.S.). The color values were determined between 7:45 and 8:30 a.m. on Apr. 26, 1990 under 600 foot candles of light intensity at Encinitas, Calif.

Classification: Alstroemeria cv. Margarita.
Commercial: Alstroemeria.

PLANT

Form: Cut flower.
Height: Approximately 104 cm. at time of harvest.
Propagation: Originates from rhizomes.
Growth habit: Excellent.
Foliage:
- *Quantity.*—21 leaves per stem.
- *Size of leaf.*—Approximately 17.5 cm. ×3.0 cm.
- *Shape of leaf.*—Lanceolate.
- *Color.*—Upper side, green 137A; under side green 137B.

Rhizomes:
- *Color.*—White, 155B.
- *Size.*—1 cm.×1 cm. at growing tip.

INFLORESCENCE

Bud:
- *Form.*—Indeterminate.
- *Diameter.*—Approximately 1.4 cm.
- *Length.*—Approximately 4.1 cm.
- *Calyx.*—Approximately 4.6 mm.
- *Peduncle.*—Length, 3 cm.
- *Color.*—Green, 137B.

Flower:
- *Size.*—Approximately 5 cm. in diameter.
- *Borne.*—5 flowers per umbel.
- *Blooming habit.*—Saleable flowering stems are ready in early December from rhizome cuttings planted approximately September 1.
- *Shape.*—Asymmetrical.
- *Color.*—Generally, the upper petals are heavily streaked, while the lower petal shows fewer, random streaks. The sepals possess a green tip which is visible on both the upper and under surfaces. A yellow spot is found on the upper petals. Upper surface: Main color, red-purple 62A. Cheek, red-purple 63B. Under surface: Main color, red-purple 62A. Cheek, red-purple 61C. Other notations: Streaks (on upper two petals): Grayed-purple 187A. Yellow spot: Yellow 4A. Green tip: Green 143A. White area around green tip and upper petals: White 155C.
- *Peduncle.*—Length, 6.3 cm.; color, green 137B.
- *Lasting quality.*—Cut flowers last 14 days after harvest.

REPRODUCTIVE ORGANS

Stamens:
- *Number.*—6.

Anthers:
- *Color.*—Grayed-green 195A.

Filaments:
- *Color.*—Red-purple 62A.

Pistils:
- *Number.*—1.
- *Color.*—Red-purple 62A.

Stigma:
- *Color.*—Red-purple 62A.

I claim:

1. A new and distinct cultivar of Alstroemeria plant named Margarita, as illustrated and described.

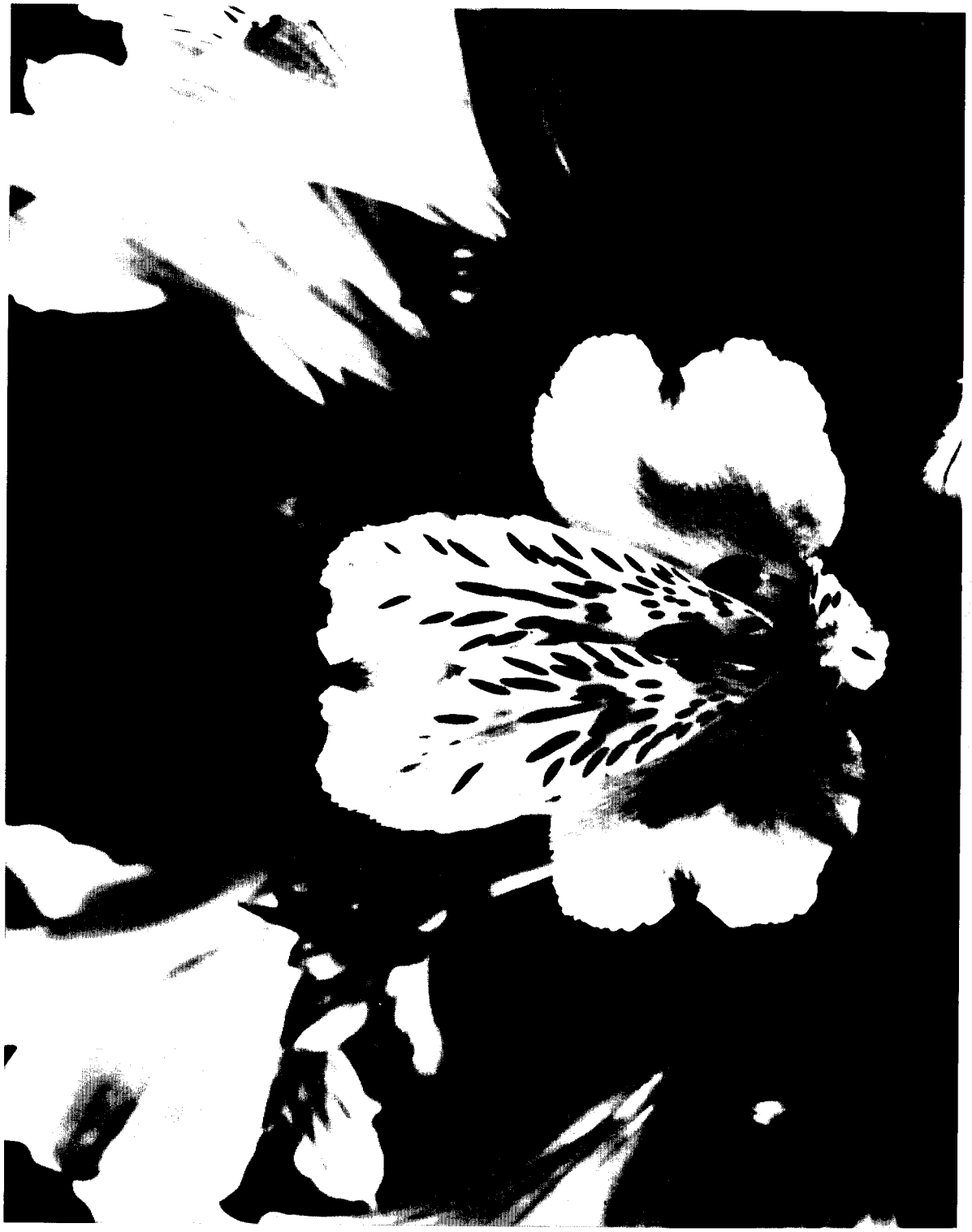

* * * * *